(12) United States Patent
Juergens

(10) Patent No.: US 10,667,672 B2
(45) Date of Patent: Jun. 2, 2020

(54) ENDOSCOPE

(71) Applicant: OLYMPUS WINTER & IBE GMBH, Hamburg (DE)

(72) Inventor: Thorsten Juergens, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 0 days.

(21) Appl. No.: 16/466,055

(22) PCT Filed: Nov. 8, 2017

(86) PCT No.: PCT/EP2017/078627
§ 371 (c)(1),
(2) Date: Jun. 3, 2019

(87) PCT Pub. No.: WO2018/109396
PCT Pub. Date: Jun. 21, 2018

(65) Prior Publication Data
US 2020/0060522 A1 Feb. 27, 2020

(30) Foreign Application Priority Data

Dec. 16, 2016 (DE) .......................... 10 2016 124 731

(51) Int. Cl.
| | |
|---|---|
| A61B 1/00 | (2006.01) |
| A61B 1/07 | (2006.01) |
| F21V 8/00 | (2006.01) |
| G02B 6/26 | (2006.01) |
| G02B 6/44 | (2006.01) |

(52) U.S. Cl.
CPC ............ *A61B 1/00126* (2013.01); *A61B 1/07* (2013.01); *G02B 6/0008* (2013.01); *G02B 6/262* (2013.01); *G02B 6/443* (2013.01)

(58) Field of Classification Search
None
See application file for complete search history.

(56) References Cited

U.S. PATENT DOCUMENTS 5,193,135 A * 3/1993 Miyagi .............. G02B 23/2469
385/117
6,389,205 B1 5/2002 Mueckner et al.
(Continued)

FOREIGN PATENT DOCUMENTS

| DE | 199 47 812 A1 | 5/2001 |
|---|---|---|
| JP | 3290700 B2 | 6/2002 |

OTHER PUBLICATIONS

International Search Report and Written Opinion dated Feb. 14, 2018 received in PCT/EP2017/078627.

*Primary Examiner* — Ashok Patel
(74) *Attorney, Agent, or Firm* — Scully, Scott, Murphy & Presser, P.C.

(57) ABSTRACT

An endoscope including: a main body; a shaft; and an optical fiber bundle extending through the shaft from the main body to a distal end of the shaft, wherein the optical fiber bundle terminates at the distal end of the shaft at an illumination exit, and the optical fiber bundle terminates at the main body at a light-guiding connector for attachment of an optical cable, and the light-guiding connector is configured to reduce an absorption, by a material of the light-guiding connector, of light that cannot be coupled from the optical cable into the optical fiber bundle.

10 Claims, 3 Drawing Sheets

(56) References Cited

U.S. PATENT DOCUMENTS

2002/0089586 A1* 7/2002 Suzuki .............. A61B 1/00165
                                                               348/68
2005/0192479 A1* 9/2005 Forster .................. G02B 23/26
                                                               600/182

* cited by examiner

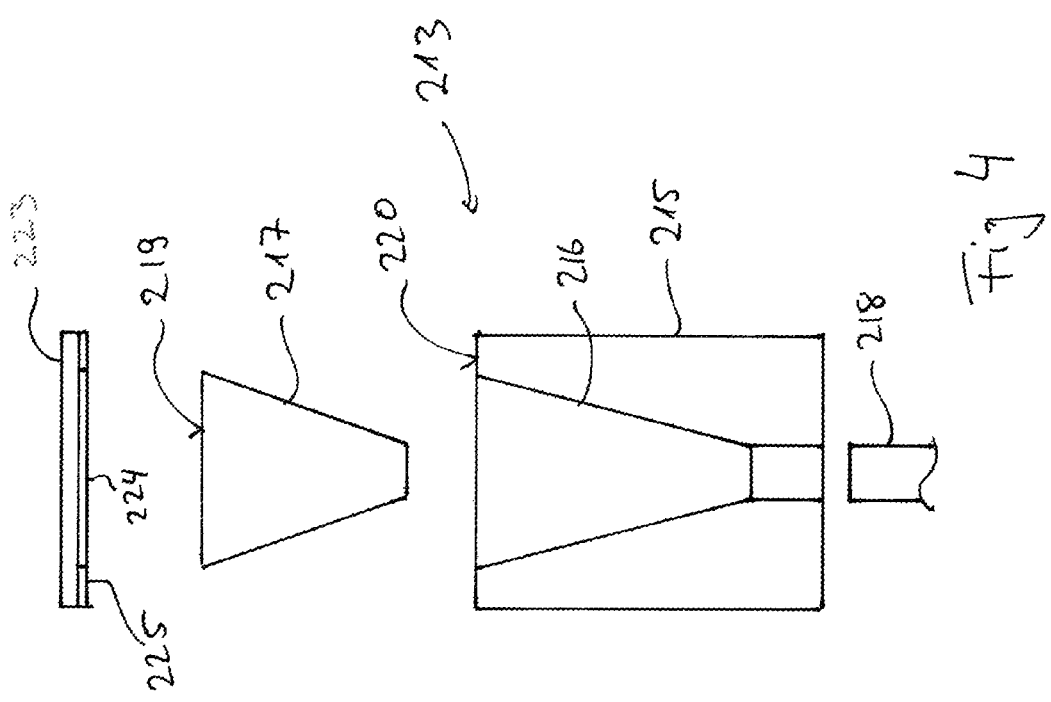

ENDOSCOPE

CROSS-REFERENCE TO RELATED APPLICATION

The present application is based upon and claims the benefit of priority from PCT/EP2017/078627 filed on Nov. 8, 2017, which claims benefit to DE 10 2016 124 731.6 filed on Dec. 16, 2016, the entire contents of each of which are incorporated herein by reference.

BACKGROUND

Field

The present disclosure relates to an endoscope with a main body, a shaft, and an optical fiber bundle extending through the shaft from the main body to a distal end of the shaft, wherein the optical fiber bundle terminates at the distal end of the shaft at an illumination exit, and the optical fiber bundle terminates at the main body at a light-guiding connector piece for attachment of an optical cable.

Prior Art

For some time, corresponding endoscopes have been used successfully for optical examination of cavities that are difficult to access in technical installations or in animal or human patients. In these cases, the endoscope is used to capture an image of the inner surface of the cavity and to make this image available outside of the cavity. The illumination is provided via an optical fiber bundle extending through the interior of the endoscope. In many cases, the light source used for illumination is configured as a separate appliance, and the light is then conveyed to the endoscope via an optical cable.

To achieve the greatest possible flexibility in the use of endoscopes, the optical cable is often configured for releasable connection to the endoscope. For this purpose, the endoscope has a light-guiding connector piece onto which the optical cable is plugged and fixed. It is in most cases fixed via standardized devices such as bayonet couplings, snap-fit couplings or threads.

The optical fiber bundle can be routed directly to an end face of the light-guiding connector piece. However, use is often made of a fiber cone for adapting the numerical aperture between the optical fibers of the optical cable and the optical fibers of the optical fiber bundle.

At the distal end of the shaft, the optical fiber bundle can be guided directly to an illumination exit. In many endoscopes, additional optical elements for adapting the light exit direction or the intensity distribution, e.g. lenses, mirrors, prisms or fused fiber elements, are provided between the optical fiber bundle and the illumination exit.

A large number of special endoscopes have been developed for different uses, said endoscopes differing, for example, in terms of shaft diameter, shaft length and viewing direction. Depending on the design and the particular use, the optical fiber bundles routed through the endoscopes have different numbers of optical fibers and therefore also different diameters.

To avoid having to keep a large number of different optical cables in stock at the same time, endoscopes are used jointly with a small number of standardized optical cables. To ensure at all times a complete illumination of the optical fiber bundle routed through the endoscope, the optical cables always have a light-guiding cross section that is larger than or the same as the cross-sectional surface area of the optical fiber bundle available at the light-guiding connector piece.

If an endoscope is now used with an optical cable whose light-guiding cross section is greater than the cross-sectional surface area of the optical fiber bundle available at the light-guiding connector piece, some of the illumination light is not coupled into the optical fiber bundle but instead strikes the material of the light-guiding connector piece and is here absorbed to a large extent. This leads to heating of the main body of the endoscope, which is undesirable.

In modern endoscopy systems, the problem is heightened by the fact that the use of increasingly higher image resolutions requires increased illumination intensity. This also results in an increase in the amount of energy absorbed at deviations in cross section.

SUMMARY

An object is therefore to make available an endoscope which is improved in respect of the problems described.

According to an embodiment, such object is achieved by an endoscope with a main body, a shaft, and an optical fiber bundle extending through the shaft from the main body to a distal end of the shaft, wherein the optical fiber bundle terminates at the distal end of the shaft at an illumination exit, and the optical fiber bundle terminates at the main body at a light-guiding connector piece for attachment of an optical cable, wherein the light-guiding connector piece is configured to reduce an absorption, by the material of the light-guiding connector piece, of light that cannot be coupled from the optical cable into the optical fiber bundle. Through the reduced absorption in the material of the light-guiding connector piece, the undesired heating of the main body is reduced.

In an embodiment of an endoscope, the end face of the light-guiding connector piece can comprise a coupling surface through which light can be coupled into the optical fiber bundle, and moreover a blind surface through which light cannot be coupled into the optical fiber bundle, and the blind surface is reflective. As a result of the reflective blind surface, light emitted from the optical cable in the region of the blind surface is reflected and guided back into the optical cable. The light thus returns to the light source, where it is likewise absorbed. However, the heating caused by this absorption in the region of the light source is much less disruptive than heating of the main body of the endoscope.

The blind surface, in a wavelength range from 350 nm to 950 nm, can have a reflectance of greater than 85%, greater than 90%, or greater than 95%. This is to be understood as meaning, within the context of this disclosure, that the blind surface has at least the indicated reflectance at each wavelength in the stated wavelength range.

According to an embodiment, the light-guiding connector piece can comprise a sleeve enveloping the optical fiber bundle, and the end face of the sleeve can be provided with a reflective coating.

The reflective coating can be lacquer or can comprise a lacquer. For example, a thin layer of a highly reflective metal can be vapor-deposited on the end face of the sleeve, which layer is in turn covered by a thin layer of a protective lacquer.

In another embodiment, the end face of the light-guiding connector piece can comprise a cover glass, which has a reflective coating in the region of the blind surface. In this case, the reflective coating can be applied to the side of the cover glass facing in the direction of the light-guiding connector piece, such that it is protected against mechanical damage when mounting or removing the optical cable.

Moreover, the cover glass can have a reflection-reducing coating in the region of the coupling surface. In this way, the efficiency of the light coupling is optimized at the same time.

The reflective and/or the reflection-reducing coating of the cover glass can be, for example, a multilayered dielectric coating. By means of such coatings, high transmittance or reflectance can be achieved over large wavelength ranges.

BRIEF DESCRIPTION OF THE DRAWINGS

The embodiments are explained below on the basis of a number of examples in the figures, in which:

FIG. 4 illustrates an exploded view of a further light-guiding connector piece.

DETAILED DESCRIPTION

Figure 1:
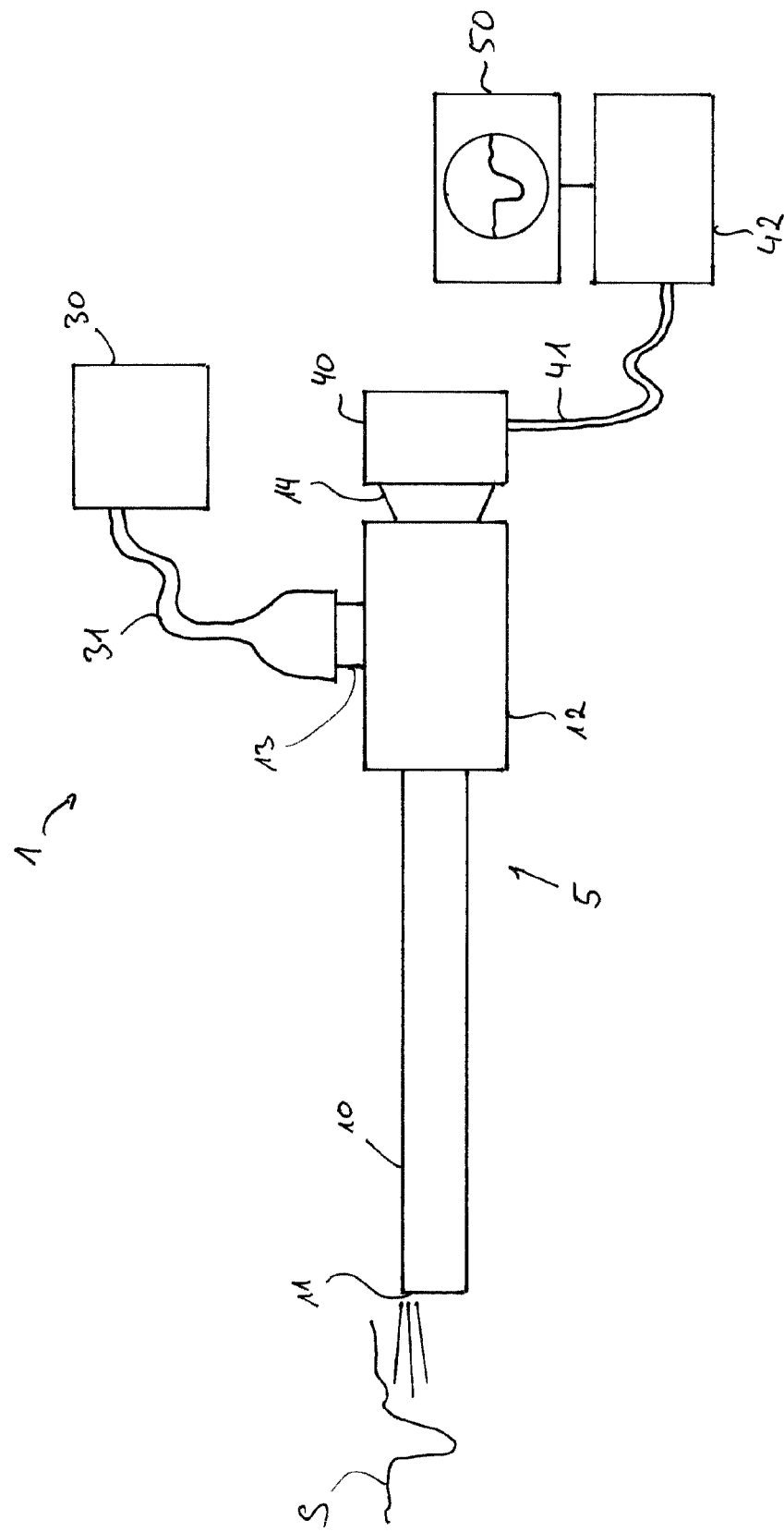
FIG. 1 illustrates an endoscopy system.

FIG. 1 shows an endoscopy system with an endoscope 5. The endoscope 5 comprises a shaft 10 with an illumination exit 11, a main body 12, a light-guiding connector piece 13 and an eyepiece cup 14.

A light source 30 is connected to the endoscope 5 via an optical cable 31. For this purpose, the optical cable 31 is plugged onto the light-guiding connector piece 13. Light from the light source 30 is coupled via the optical cable 31 into an optical fiber bundle (not shown) in the endoscope 5 and is guided in this optical fiber bundle to the illumination exit 11 at the distal end of the shaft 10. There, the light is radiated in the direction of an anatomical structure S.

The light reflected from the anatomical structure S is collected via an objective lens (not shown) at the distal end of the shaft 10 and is guided via an image carrier (likewise not shown), which can be a relay lens system or an image fiber bundle, to the eyepiece cup 14. There, it is converted into a video image by a camera 40 mounted on the eyepiece cup 14 and is guided via a video cable 41 to an image processor 42, which carries the video image to a monitor 50 for display.

Figure 2:
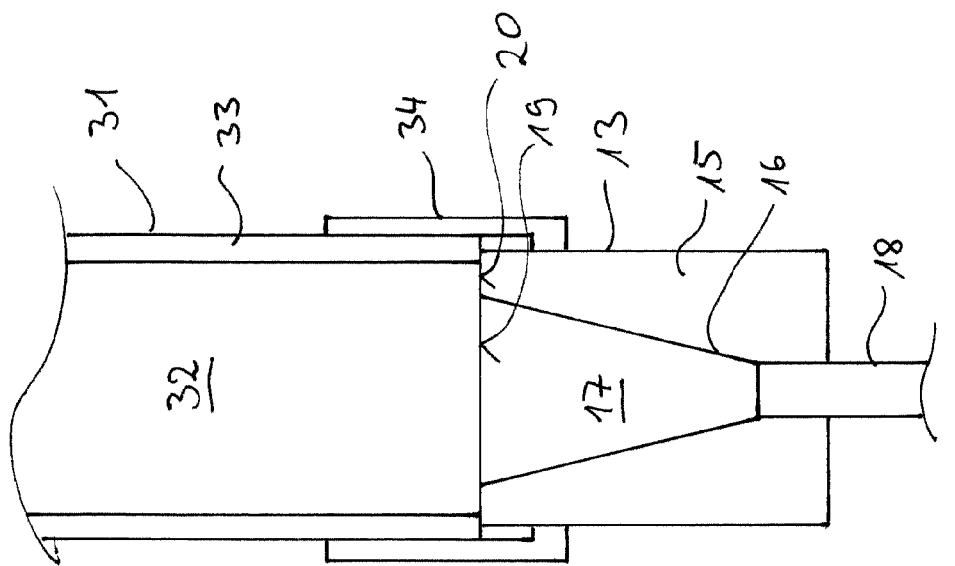
FIG. 2 illustrates a light-guiding connector piece with attached optical cable.

FIG. 2 shows a schematic sectional view of the light-guiding connector piece 13 of the endoscope 5. It consists of a sleeve 15 with a conically widening bore 16, into which a fiber cone 17 is clamped. Adjacent to the fiber cone 17, an optical fiber bundle 18 is inserted into the bore 16.

The optical cable 31 is fitted onto the light-guiding connector piece 13. The optical cable comprises a light-guiding cross section 32 of individual optical fibers which, for the sake of clarity, are not shown. The optical cable is surrounded by a protective tube 33, which protects the fibers from mechanical damage. A plug-on sleeve 34 is secured on the protective tube 33, with which plug-on sleeve 34 the optical cable 31 is plugged onto the light-guiding connector piece 13 and fixed.

Light from the optical cable 31 is coupled into the fiber cone 17 and is forwarded from the latter to the optical fiber bundle 18. The conical shape of the fiber cone ensures adaptation of the numerical aperture of the fibers of the optical cable 31 to the numerical aperture of the fibers of the optical fiber bundle 18.

The end face of the fiber cone 17, facing in the direction of the optical cable 31, constitutes a coupling surface 19 through which light can be coupled into the fiber cone 17 and thus into the optical fiber bundle 18. By contrast, the end face of the sleeve 15, facing in the direction of the optical cable 31, constitutes an annular blind surface 20 through which light cannot be coupled.

A large part of the light emitted from the optical cable 31 in the region of the blind surface 20 is absorbed by the sleeve 15, such that the latter heats up. In the example shown, the diameter of the light-guiding cross section 32 of the optical cable 31 is approximately 50% larger than the diameter of the coupling surface 19. In this arrangement, approximately 50% of the light transported through the optical cable 31 is already lost. It hits the blind surface 20 and is to a large extent absorbed there and contributes only to heating of the sleeve 15 and therefore of the main body 12.

Figure 3:
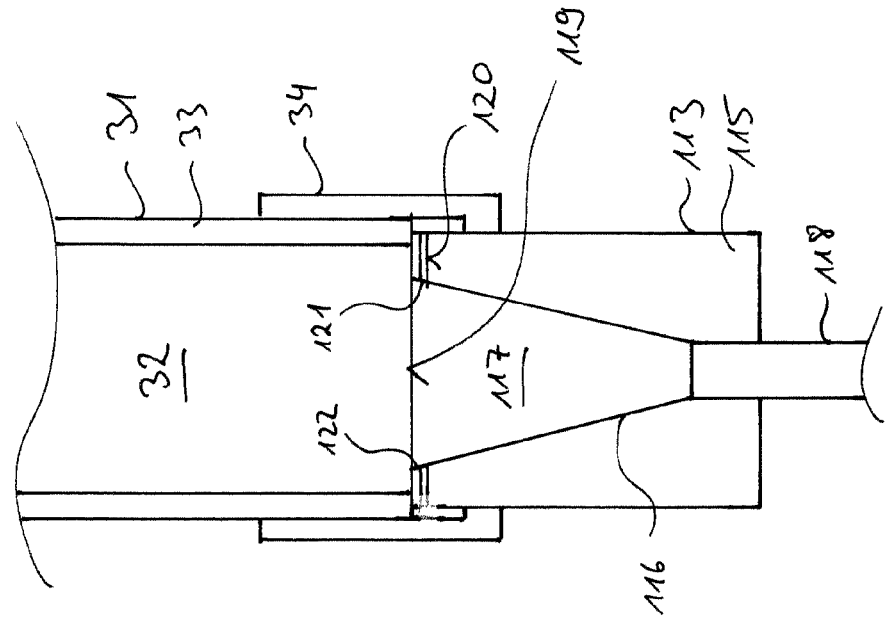
FIG. 3 illustrates a further light-guiding connector piece with attached optical cable.

FIG. 3 shows a modified light-guiding connector piece 113 of an endoscope according to an embodiment. The light-guiding connector piece 113 corresponds substantially to the light-guiding connector piece 13 of FIG. 2. Therefore, components corresponding to each other are designated by a reference sign increased by 100 and are not described all over again. The optical cable 31 is again fitted onto the light-guiding connector piece 113.

Here, a highly reflective metal layer 121 and a protective lacquer layer 122 are applied to the blind surface 120 of the sleeve 115. Light emitted from the optical cable 31 in the region of the blind surface 120 now hits the reflective surface 121 and is reflected back in the direction of the optical cable 31. Except for minor coupling losses, this light is transported through the optical cable 31 back to the light source 30 and emitted there. Although the reflected light is ultimately converted to heat here too, this is much less critical in the region of the light source 30 than in the region of the light-guiding connector piece 113.

The metal layer 121 can be a silver layer, for example. With such a layer, it is possible to achieve reflectance of more than 85% over a broad wavelength range.

FIG. 4 shows an exploded view of a further light-guiding connector piece 213 of an endoscope. The light-guiding connector piece 213 once again comprises a sleeve 215 with conical bore 216. A fiber cone 217 is inserted into the bore from one side, and the end of an optical fiber bundle 218 disposed in the endoscope is inserted from the other side. A cover glass 223 is arranged on the end face of the sleeve 215 and of the fiber cone 217, and a reflection-reducing layer 224 is applied to the cover glass 223 on its side directed toward the sleeve 215 in the region of the coupling surface 219. In the region of the blind surface 220, a reflective layer 225 is applied to the cover glass 223.

The function of the light-guiding connector piece 213 corresponds substantially to that of the light-guiding connector piece 113 from FIG. 3 and therefore does not require a separate explanation.

The coatings 224, 225 can be configured as multilayered dielectric coatings, in order to ensure a sufficient efficiency over the broadest possible wavelength range. For the reflective layer 225, a reflectance of more than 95% can be achieved over a broad wavelength range with a dielectric coating.

The reflective layers in all of the illustrative embodiments are arranged such that the desired reflectance is achieved as far as possible in the entire spectrum emitted from the light source. This comprises the entire range of the visible light, but also the near UV and IR range. These wavelength ranges are required, such as for fluorescence examinations and are therefore also generated by the light source. Accordingly, the absorption of the corresponding spectral parts of the light in the light-guiding connector piece should also be avoided.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

That is claimed is:

1. An endoscope comprising:
   a main body;
   a shaft having a distal end;
   an optical fiber bundle extending through the shaft from the main body to the distal end of the shaft, the optical fiber bundle terminating at the distal end of the shaft at an illumination exit; and
   a light guiding connector disposed in the main body at the illumination exit of the optical fiber bundle, the light guiding connector being configured to attach to an optical cable;
   wherein the light-guiding connector comprises a material configured to reduce an absorption of light that cannot be coupled from the optical cable into the optical fiber bundle.

2. The endoscope as claimed in claim 1, wherein the light guide connector further comprises an end face having a coupling surface through which light can be coupled into the optical fiber bundle, the end face of the light-guiding connector comprises a blind surface through which light cannot be coupled into the optical fiber bundle, and the blind surface having the material, the material being reflective.

3. The endoscope as claimed in claim 2, wherein the material, in a wavelength range from 350 nm to 950 nm, has a reflectance of greater than 85%.

4. The endoscope as claimed in claim 2, wherein the light-guiding connector comprises a sleeve enveloping the optical fiber bundle, and the material is provided on an end face of the sleeve, the material being a reflective coating.

5. The endoscope as claimed in claim 4, wherein the reflective coating comprises a lacquer.

6. The endoscope as claimed in claim 2, wherein the end face of the light-guiding connector comprises a cover glass, the material being applied to the cover glass in a region of the blind surface.

7. The endoscope as claimed in claim 6, wherein the cover glass has a reflection-reducing coating in the region of the coupling surface.

8. The endoscope as claimed in claim 6, wherein the material is a multilayered dielectric coating.

9. The endoscope as claimed in claim 2, wherein the material on the blind surface, in a wavelength range from 350 nm to 950 nm, has a reflectance of greater than 90%.

10. The endoscope as claimed in claim 2, wherein the material on the blind surface, in a wavelength range from 350 nm to 950 nm, has a reflectance of greater than 95%.

* * * * *